United States Patent [19]

Klopries et al.

[11] Patent Number: 5,668,077
[45] Date of Patent: Sep. 16, 1997

[54] SILVER CATALYST FOR THE OXIDATION OF ETHYLENE OXIDE

[75] Inventors: Burkhard Klopries, Bottrop, Germany; Harald Metz, Greensboro, N.C.; Wilma Dibowski, Marl, Germany; Dietmar Kyewski, Haltern, Germany; Jürgen Pospiech, Marl, Germany

[73] Assignee: Huels Aktiengesellschaft, Marl, Germany

[21] Appl. No.: 623,775

[22] Filed: Mar. 29, 1996

Related U.S. Application Data

[63] Continuation of Ser. No. 224,526, Apr. 7, 1994, abandoned.

[30] Foreign Application Priority Data

Apr. 8, 1993 [DE] Germany .................. 43 11 608.6

[51] Int. Cl.$^6$ ........................................ B01J 23/48
[52] U.S. Cl. ........................................ 502/347
[58] Field of Search .................... 502/344, 347

[56] References Cited

U.S. PATENT DOCUMENTS

| | | |
|---|---|---|
| 3,702,259 | 11/1972 | Nielsen . |
| 4,012,425 | 3/1977 | Nielsen et al. . |
| 4,097,414 | 6/1978 | Cavitt . |
| 4,169,883 | 10/1979 | Murrell et al. . |
| 4,356,312 | 10/1982 | Nielsen et al. . |
| 4,523,923 | 6/1985 | Büchel et al. . |
| 4,760,042 | 7/1988 | Armstrong . |
| 5,063,195 | 11/1991 | Jin et al. . |

FOREIGN PATENT DOCUMENTS

| | | |
|---|---|---|
| 0 091 165 | 10/1983 | European Pat. Off. . |
| 0 229 465 | 7/1987 | European Pat. Off. . |
| 0 172 565 | 3/1991 | European Pat. Off. . |
| 0 428 845 | 5/1991 | European Pat. Off. . |
| 2 244 566 | 4/1975 | France . |
| 2 495 958 | 6/1982 | France . |

OTHER PUBLICATIONS

Sune Svanberg, "Atomic and Molecular Spectroscopy: Basic Aspects and Practical Applications," 2nd Edition, 1991, pp. 75–83.

Journal of the American Chemical Society, vol. 73, 1951, pp. 373–380, Elliott Barrett, et al., "The Determination of Pore Volume and Area Distributions in Porous Substances. I. Computations from Nitrogen Isotherms".

Journal of the American Institute of Chemical Engineers, vol. 143, No. 70, 1974, pp. 1–4, Earl Beaver, "Mechanical Testing of Extruded, Tableted, and Ring–Formed Catalysts".

Powder Metallurgy International, vol. 18, No. 1, 1986, pp. 12–16, Erich Robens, "The Measurement of Specific Surface Area and Pore Size Distribution of Powders".

*Primary Examiner*—Michael Lewis
*Assistant Examiner*—Thomas G. Dunn, Jr.
*Attorney, Agent, or Firm*—Oblon, Spivak, McClelland, Maier & Neustadt, P.C.

[57] ABSTRACT

The invention relates to a silver catalyst for the partial oxidation of ethylene with molecular oxygen in the gas phase to form ethylene oxide and a process for preparing ethylene oxide using this catalyst. The catalyst is superior to comparable catalysts of the prior art through an increased selectivity (at high activity) and/or a more favorable ageing behavior. The process for preparing ethylene oxide is distinguished by improved economics.

19 Claims, No Drawings

SILVER CATALYST FOR THE OXIDATION OF ETHYLENE OXIDE

This application is a continuation of application Ser. No. 08/224,526, filed on Apr. 7, 1994, now abandoned.

BACKGROUND OF THE INVENTION

1. Field of the Invention

The present invention pertains to silver catalysts suitable for the manufacture of ethylene oxide by the partial oxidation of ethylene in the gas phase. More particularly, the present invention pertains to silver catalysts supported on a macroporous ceramic support in which the silver particle size is related to the macropore size.

2. Description of the Related Art

Supported silver catalysts for use in the partial oxidation of ethylene in the gas phase such that the average diameter of the silver particles is less than a fixed fraction of the number-average pore diameter of the support are known (see for example EP-A 0 172 565 and EP-A 0 428 845). The silver catalysts of the prior art display high selectivity (at high activity) and favorable ageing behavior, characteristics which determine the economics of the manufacture of ethylene oxide. In view of the increased competition between ethylene oxide producers there is yet a need for an improved silver catalyst having even greater selectivity (at high activity) and/or more favorable ageing behavior, and thus improved economics for ethylene oxide manufacture.

OBJECTS OF THE INVENTION

It is thus an object of the invention to provide a silver catalyst which is superior to the silver catalysts of the prior art in respect of selectivity (at high activity) and/or ageing behavior and thus allow an improvement in the economics of the process of ethylene oxide manufacture.

These, and other objects are surprisingly achieved in the manner indicated herein.

SUMMARY OF THE INVENTION

The invention provides for a silver catalyst containing from 10 to about 25 weight percent silver particles on a macroporous ceramic support having a pore volume in the untreated condition of greater than 0.35 cm$^3$/g, wherein the silver particles satisfy the condition that the average silver particle diameter is less than about 0.4 times the number-average pore diameter of the macroporous ceramic support, and further, that silver particles located in the outer surface of the finished catalyst form essentially no silver bridges, such that the finished catalyst displays the high electrical resistance characteristic of an insulator.

DESCRIPTION OF THE PREFERRED EMBODIMENTS

The invention thus provides a silver catalyst having a silver content of from 10 to 25% by weight, preferably from 15 to 22% by weight, based on the finished catalyst, for the partial oxidation of ethylene with molecular oxygen in the gas phase to form ethylene oxide, the silver being present as particles which are situated on a porous, nonacidic, heat resistant, ceramic support and have a number-average diameter of from 0.05 to <0.4 µm, preferably from 0.05 to <0.3 µm, determined by scanning electron microscopy (SEM). The determination is carried out by first breaking through the finished supported silver catalyst, which is generally annular in shape. The whole cross section is then tested. The invention further provides a process for the partial oxidation of ethylene with molecular oxygen in the gas phase to form ethylene oxide, using the silver catalyst. The silver catalyst is characterized by the additional features below.

The support is macroporous. According to IUPAC, macropores are pores having a diameter of >50 nm. Pores having a diameter between 2 nm and 50 nm are described as mesopores. The macroporosity of the support is characterized by a pore volume of >0.35 cm$^3$/g, preferably >0.40 cm$^3$/g of the untreated support, determined by Hg porosimetry at a pressure rising to 2000 bar, i.e. by the lower limit of the pore volume. This method measures the pore volumes of the macropores and in part also of the mesopores (E. Robens, "The Measurement of Specific Surface Area and Pore Size Distribution of Powders", in *Powder Metallurgy International*, Vol. 18/1 (1986), pages 12 to 16). The macroporosity of the support with respect to the upper limit of the pore volume is characterized by the lateral fracture strength of the finished catalyst being not less than 20N (E. R. Beaver, "Mechanical Testing of Extruded, Tableted and Ring-formed Catalysts," *American Institute of Chemical Engineers, Symposium Series*, Vol. 143/70 (1974), pages 1 to 4). Surprisingly, the lateral fracture strength of the finished catalyst is significantly higher than that of the untreated support.

The average diameter of the silver particles should satisfy the additional condition of being less than about 0.4 times, preferably less than about 0.3 times the number-average pore diameter of the untreated support. The average pore diameter is derived from the pore radius distribution determined by Hg porosimetry at a pressure rising to 2000 bar. This method measures the macropores and in part also the mesopores. The untreated support has an average pore diameter of ≧1 µm.

The silver particles in the outer surface of the finished catalyst should form essentially no silver bridges, so that the finished catalyst behaves like an insulator with high electrical resistance. For testing, a high-ohmic resistance measuring apparatus (measuring range from 0 to 200 MΩ) having two point electrodes at a separation of 1 mm is suitable. The electrodes are run over the surface of the catalyst particles. The silver catalyst fails the test if the resistance measuring apparatus shows a value in the indicated measuring range. The silver catalyst of EP-A 0 428 845, for example, fails the test. Therefore, a suitable silver catalyst has an electrical resistance of greater than 200 MΩ with the described measuring arrangement.

The silver particles generally have a spherical shape. They can be clearly recognized in SEM micrographs at a magnification of 50,000×. It is disadvantageous for the silver particles to have essentially point contact with the surface of the support which is in turn structured. If a tangent is drawn on the image of the silver particle to the boundary of the silver particle and surface of the support, an angle can be measured between the tangent and the surface of the support. This angle is defined as the contact angle. In the case of essentially point contact, it is <30°. A small contact angle has an unfavorable effect on the ageing behavior of the silver catalyst. The contact angle preferably has an average value >30°, in particular >50°. The test is carried out by first breaking through the finished silver catalyst. The whole cross section is then examined. Surprisingly, a large contact angle can be set by doping the metallic silver with a cationic component selected from the group of compounds of Li, Na, K, Cs, Mg, Ca, Ba, Ti, V, Cr and Re. Preference is given to a silver catalyst in which the contact angle is adjusted by doping the silver with a cesium compound.

A preferred support has a surface area of the macropores of >0.8 m²/g Of the untreated support, determined by Hg porosimetry at a pressure rising to 2000 bar.

To give a high selectivity of the silver catalyst, the catalyst support has as few micropores and mesopores as possible. According to IUPAC, the term micropore means pores having a diameter between 0.6 nm and 2 m. The pore volume of the catalyst support in the micropore and mesopore range is determined by the physisorption isotherm of nitrogen at the temperature of liquid nitrogen. The method is carried out in accordance with DIN 66 131 (BET method). The evaluation is carried out in accordance with the method of Barret, Joyner and Halenda from the desorption isotherm (*J. Am. Chem. Soc.* 73 (1951), page 373). For a high selectivity of the silver catalyst, the micropore volume of the support determined by BET should be as small as possible. A preferred support has a BET pore volume of <0.03, preferably <0.02, cm³/g, of the untreated support. By the term "untreated" support is meant the macroporous ceramic support prior to impregnation with silver as disclosed herein.

A preferred support comprises greater than 80% by weight, more particularly greater than 90% by weight, of Al₂O₃, in particular α-Al₂O₃. The silver particles should be uniformly distributed on the surface of the support which is freely accessible to gases. The uniformity of the distribution of the silver particles on the surface of the support which is freely accessible to gases is characterized by the average degree of coating with silver, determined by the ESCA method, of the surface of the support freely accessible to gases. The degree of coating is defined by the quotient $$\frac{Ag\,(at\,\%)}{Ag\,(at\,\%) + Al\,(at\,\%)},$$

where at % means atom percent.

The test is carried out by first breaking through the finished silver catalyst. The fractured surfaces of a plurality of catalyst particles are irradiated with X-rays, the surfaces being circular areas having a diameter of 0.33 mm a) in the middle of the fracture surface ("in the inner region") and b) at a distance of 0.3 mm from the outer boundaries of the fracture surfaces ("in the boundary region"). The electrons ejected from the surface have various energies depending on the type of elements. The intensity of the resultant electron radiation is a measure of the proportion of the element in the surface (S. Svanberg, *Atomic and Molecular Spectroscopy, Basic Aspects and Practical Applications*, Springer Verlag, 1991). The average degree of coating should be >0.3, in particular >0.4, for both measurement condition a) and measurement condition b).

The silver catalyst is produced by basically known methods, i.e. generally via the following process steps: impregnation of the support at reduced pressure with an aqueous (colloidal) solution of a silver salt, the surface tension of which is advantageously adjusted to <50 mN/m by a suitable surfactant, drying and pyrolysis. The metallic silver is deposited on the support in the latter process steps. A suitable solution is, for example, a solution of a silver lactate or silver oxalate/amine complex, the surface tension of which solution has been adjusted with a laurylamine ethoxylate (10 mol of ethylene oxide/mol of laurylamine). Suitable complexing amines are, for example, monoethanolamine and ethylenediamine. After drying, a second impregnation and second drying may follow. The drying is generally carried out at from 105° to 150° C. The pyrolysis is carried out by heating at a heating rate of ≧1° C./s to 180° C. It is completed by final activation at ≧240° C.

According to the teachings of the present invention, it is possible to produce silver catalysts having a large silver surface area. The resulting catalysts correspondingly have a high activity. In a process for preparing ethylene oxide with the silver catalyst, this allows the use of a comparatively low reaction temperature and, correspondingly, the establishing of a comparatively high oxygen content in the recirculated gas. The low reaction temperature, which generally does not exceed 235° C., preferably 225° C., has a favorable effect on the ageing behavior.

Having generally described this invention, a further understanding can be obtained by reference to certain specific examples which are provided herein for purposes of illustration only and are not intended to be limiting unless otherwise specified. In the Examples, percent (%) means % by weight.

EXAMPLE 1

(Production of the silver catalyst)

An annular catalyst support with the following characteristics was used:

| | |
|---|---|
| External diameter/internal diameter/height [mm] | 6.5/3/6 |
| Bulk density [g/l] | 747 |
| Water absorption capacity, based on the dry support [%] | ca. 50 |
| Lateral fracture strength [N] | 33 |
| Al₂O₃ content [%]* | >97 |
| Volume of the macropores [cm³/g]** | 0.47 |
| Surface area of the macropores [m²/g]** | 1.03 |
| Number-average diameter of the macropores [μm] | 4.1 |
| Volume of the micropores and mesopores [cm³/g]*** | <0.01 |

*present as α-Al₂O₃
**determined by Hg porosimetry with the Porosimeter 2000 from Carlo Erba
***determined by the BET method To a solution of 1778 g of silver nitrate in 1.7 l of fully deionized water were added 1.6 l of a 25 wt. % aqueous sodium hydroxide solution. The precipitated silver hydroxide was isolated by filtration, washed free of nitrate with fully deionized water, and stirred with fully deionized water to form a slurry. 692 g of crystalline oxalic acid were added with cooling. The silver oxalate obtained was admixed with 566 g of ethylenediamine, 296 g of monoethanolamine and 4.0 g of laurylamine ethoxylate (10 mol of ethylene oxide/ mol of laurylamine). To the concentrated silver oxalate/ amine complex solution so obtained were added 2436 g of the above-described dry support. The mixture was agitated by rotation in a suitable vessel and heated to about 40° C. The impregnated support was degassed by reducing the pressure until gentle boiling occurred. Subsequently the supernatant liquid was decanted and the treated support dried at from 105° to 120° C. in a stream of nitrogen. The dried catalyst was admixed with a mixture containing the previously decanted liquid and an aqueous solution of 2.84 g of CsNO₃. The impregnated support was again degassed as above at about 40° C. at reduced pressure. The treated support was then dried at from 105° to 150° C. in a stream of nitrogen. For pyrolysis, the treated support was heated at a rate of ≧1° C./s up to 210° C. and maintained at this temperature for 1 hour. During pyrolysis the support was flushed with a nitrogen/hydrogen stream containing 4% by volume of hydrogen. The characteristics of the finished silver catalyst can be found on the next page.

The finished silver catalyst so obtained has the following characteristics:

| | |
|---|---|
| Lateral fracture strength [N] | 42 |
| Electrical resistance [MΩ] | >200 |
| Silver content [%] | 20 |
| Average degree of coating (boundary region) | 0.47 |
| (interior region) | 0.46 |
| Contact angle [°] | from 50 to 60 |
| Number-average diameter of the silver particles [μm] | 0.15 |

$$\frac{\text{Average diameter of silver particles}}{\text{Average diameter of the support macropores}} = \frac{0.15 \, \mu m}{4.1 \, \mu m} = 0.037*$$

*Ratio, diameter of silver particles to diameter of macropores.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A supported silver catalyst, comprising:
    (a) a macroporous, nonacidic, heat resistant ceramic support having a number-average pore volume of greater than about 0.35 cm$^3$/g as determined by mercury porosimetry at a pressure rising to 2,000 bar, and having a number-average pore volume upper limit such that the lateral fracture strength of the finished catalyst is not less than 20N and wherein said macroporous ceramic support has a surface area of macropores of greater than about 0.8 m$^2$/g as determined by mercury porosimetry at a pressure rising to 2,000 bar;
    (b) silver particles having number-average diameters as determined by scanning electron microscopy of from about 0.05 μm to about 0.4 μm,
    wherein the average diameter of said silver particles is less than about 0.4 of the number-average macropore diameter of said macroporous support, said macropore diameter determined by mercury porosimetry at a pressure rising to 2,000 bar and being greater than or equal to about 1 μm; and
    wherein said silver particles in the outer surface of the finished catalyst form essentially no silver bridges, such that the catalyst behaves likes an insulator with high electrical resistance.

2. The catalyst of claim 1, wherein the average contact angle between silver particles and support is greater than about 30°.

3. The catalyst of claim 1, wherein the average contact angle between silver particles and support is greater than about 50°.

4. The catalyst of claim 2, wherein the contact angle is adjusted by doping the metallic silver with a cationic component selected from the group consisting of the compounds of Li, Na, K, Cs, Mg, Ca, Ba, Ti, V, Cr, and Re.

5. The catalyst of claim 3, wherein the contact angle is adjusted by doping the metallic silver with a cationic component selected from the group consisting of the compounds of Li, Na, K, Cs, Mg, Ca, Ba, Ti, V, Cr, and Re.

6. The catalyst of claim 4, wherein said doping compound is a cesium compound.

7. The catalyst of claim 5, wherein said doping compound is a cesium compound.

8. The catalyst of claim 1, wherein the macroporous ceramic support has a BET pore volume of <0.03 cm$^3$/g.

9. The catalyst of claim 2, wherein the macroporous ceramic support has a BET pore volume of <0.03 cm$^3$/g.

10. The catalyst of claim 3, wherein the macroporous ceramic support has a BET pore volume of <0.03 cm$^3$/g.

11. The catalyst of claim 4, wherein the macroporous ceramic support has a BET pore volume of <0.03 cm$^3$/g.

12. The catalyst of claim 1, wherein the macroporous ceramic support has a BET pore volume of <0.02 cm$^3$/g.

13. The catalyst of claim 2, wherein the macroporous ceramic support has a BET pore volume of <0.02 cm$^3$/g.

14. The catalyst of claim 3, wherein the macroporous ceramic support has a BET pore volume of <0.02 cm$^3$/g.

15. The catalyst of claim 4, wherein the macroporous ceramic support has a BET pore volume of <0.02 cm$^3$/g.

16. The catalyst of claim 1, wherein said support comprises greater than 80% by weight aluminum oxide.

17. The catalyst of claim 1, wherein said support comprises greater than 90% by weight aluminum oxide.

18. A supported silver catalyst, comprising:
    (a) a macroporous, nonacidic, heat resistant ceramic support having a pore volume of greater than about 0.35 cm$^3$/g as determined by mercury porosimetry at a pressure rising to 2000 bar, and having a pore volume upper limit such that the lateral fracture strength of the finished catalyst is not less than 20N;
    (b) silver particles having number-average diameters as determined by scanning electron microscopy of from about 0.05 μm to about 0.4 μm,
    wherein the average diameter of said silver particles is less than about 0.4 of the number-average macropore diameter of said macroporous support, said macropore diameter determined by mercury porosimetry at a pressure rising to 2000 bar and being greater than or equal to about 1 μm;
    wherein said silver particles in the outer surface of the finished catalyst form essentially no silver bridges, such that the catalyst behaves like an insulator with high electrical resistance;
    wherein the average contact angle between silver particles and the support is greater than about 30°;
    wherein said contact angle is adjusted by doping the metallic silver with a cationic component selected from the group consisting of the compounds of Li, Na, K, Cs, Mg, Ca, Ba, Ti, V, Cr, and Re;
    wherein the untreated macroporous support has a surface area of the macropores of greater than about 0.8 m$^2$/g and a BET pore volume of less than 0.03 cm$^3$/g; and
    wherein said untreated support comprises aluminum oxide in an amount greater than about 80 weight percent.

19. The catalyst of claim 18, wherein said contact angle is greater than about 50° C.; said cationic component is a cesium compound; said BET pore volume is less than about 0.02 cm$^3$/g; and said untreated support comprises greater than about 90 weight percent α-Al$_2$—O$_3$.

* * * * *